United States Patent [19]

Cale, Jr.

[11] 4,144,245
[45] Mar. 13, 1979

[54] 4-HYDROXYMETHYL-2-PYRROLIDI-NONES

[75] Inventor: Albert D. Cale, Jr., Mechanicsville, Va.

[73] Assignee: A. H. Robins Company, Inc., Richmond, Va.

[21] Appl. No.: 892,539

[22] Filed: Feb. 3, 1978

Related U.S. Application Data

[63] Continuation of Ser. No. 795,847, May 11, 1977, abandoned, which is a continuation-in-part of Ser. No. 615,951, Sep. 23, 1975, Pat. No. 4,119,637.

[51] Int. Cl.$^2$ ............... C07D 207/26; C07D 207/44
[52] U.S. Cl. ........................................ 260/326.5 FL
[58] Field of Search ............................. 260/326.5 FL Primary Examiner—Jose Tovar

[57] ABSTRACT

1-Hydrocarbon-3,3-diphenyl-4-hydroxymethyl-2-pyrrolidinones and methods for making them from 4,5-dihydro-3,3-diphenyl-4-hydrocarbylaminomethylfuran-2(3H)ones are disclosed. Methods for making the 4,5-dihydro-3,3-diphenyl-4-hydrocarbylaminomethylfuran-2(3H)ones are also disclosed. The novel compounds are useful intermediates for the preparation of pharmacologically active 4-(4,4-disubstitutedpiperidinylmethyl)-3,3-diphenyl-2-pyrrolidinones.

1 Claim, No Drawings

4-HYDROXYMETHYL-2-PYRROLIDINONES

This is a continuation of application Ser. No. 795,847, filed May 11, 1977, now abandoned, which application is a continuation-in-part of copending application Ser. No. 615,951 filed Sept. 23, 1975 now U.S. Pat. No. 4,119,637.

This invention relates to novel 2-pyrrolidinones and more particularly to 1-hydrocarbon-3,3-diphenyl-4-hydroxymethyl-2-pyrrolidinones having the formula:

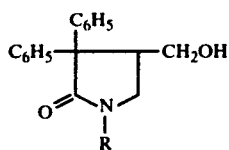

Formula I wherein R is hydrogen, lower-alkyl, lower cycloalkyl, and phenyllower alkyl.

The invention is also concerned with novel tetrahydrofuran-2-ones, especially 4,5-dihydro-3,3-diphenyl-4-hydrocarbylaminomethylfuran-2(3H)ones having the formula:

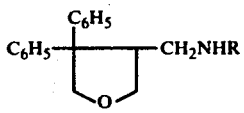

Formula II wherein R is lower alkyl, lower cycloalkyl and phenyllower alkyl.

The invention also relates to novel processes for preparing the novel compounds of Formulae I and II and to novel compounds which can be prepared from the compounds of Formula I.

The novel compounds of Formula I are particularly useful as intermediates for the preparation of a series of novel 4-(4-disubstituted-piperidinylalkyl)-3,3-diphenyl-2-pyrrolidinones wherein alkyl is methyl having analgetic and antidiarrheal properties disclosed in copending application Ser. No. 615,952.

The novel 4,5-dihydro-3,3-diphenyl-4-hydrocarbylaminomethylfuran-2(3H)ones of Formula II are useful as precursors for the novel 1-hydrocarbon-3,3-diphenyl-4-hydroxymethyl-2-pyrrolidinones of Formula I. The compounds also form fluosilicic acid addition salts which are useful as mothproofing agents according to U.S. Pat. Nos. 1,915,334 and 2,075,359.

It is, accordingly, an object of the present invention to provide novel and useful 1-hydrocarbon-3,3-diphenyl-4-hydroxymethyl-2-pyrrolidinones. A further object is to provide novel and useful 4,5-dihydro-3,3-diphenyl-4-hydrocarbylaminomethylfuran-2(3H)ones. A still further object is to provide novel processes for the preparation of the novel 1-hydrocarbon 3,3-diphenyl-4-hydroxymethyl-2-pyrrolidinones and 4,5-dihydro-3,3-diphenyl-4-hydrocarbylaminomethylfuran-2(3H)ones. Other objects of the invention will be apparent to one skilled in the art, and still other objects will become apparent hereinafter from the description which follows and the appended claims.

The term "lower-alkyl" as used herein includes straight and branched chain radicals of up to six carbon atoms inclusive and is exemplified by such groups as methyl, ethyl, propyl, butyl, isopropyl, isobutyl, tertiary butyl, amyl, hexyl and isohexyl.

The term "phenyllower-alkyl" as used herein includes radicals such as benzyl, phenethyl, phenpropyl and α-methylbenzyl.

The term "lower cycloalkyl" as used herein includes cycloalkyl radicals having four to eight carbon atoms such as cyclobutyl, cyclopentyl, cyclohexyl, cycloheptyl and cyclooctyl, cyclopentyl and cyclohexyl being preferred radicals.

The novel compounds of Formula I are prepared by the following procedure:

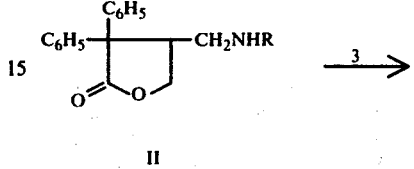

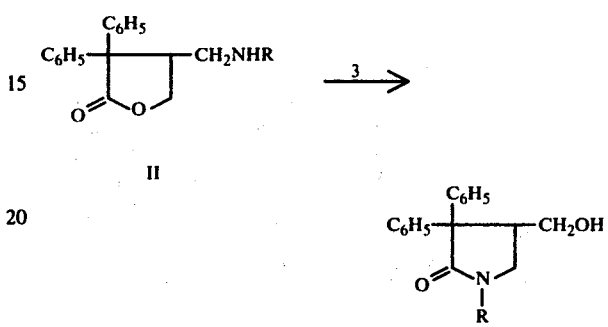

wherein R is as defined above and B is a basic catalyst.

According to the above procedure a 4,5-dihydro-3,3-diphenyl-4-hydrocarbylaminomethylfuran-2-(3H)one II is mixed with a catalytic amount of a strong base such as an alkali metal hydride, an alkali metal amide, an alkali metal tertiary butoxide or an alkali metal hydroxide, an alkali metal hydride being preferred, to cause intramolecular rearrangement to the 1-hydrocarbon-3,3-diphenyl-4-hydroxymethyl-2-pyrrolidinone I. The novel intramolecular rearrangement is usually carried out with the application of heat, e.g., in refluxing isooctane, benzene, toluene, or like solvent, for an extended period, e.g., of from about 10 to about 20 hours. The pyrrolidinone generally separates from the cooled reaction mixture as a crystalline solid which is isolated by filtration and is further purified by crystallization from a suitable solvent or solvents.

It has been found that the presence of the strong basic catalyst and the application of heat for an extended period of of time, while necessary to effect the foregoing rearrangement when R is a bulky radical such as isopropyl or cyclohexyl, is not necessary to effect the said foregoing rearrangement when R is a non-bulky radical, i.e., when R is methyl or hydrogen. Thus, when R is methyl as in Example 3, the furan-2(3H)one compound can be isolated by immediate conversion of the free base to the acid addition salt. However, when the furan-2(3H)one is not in an acidic environment but is allowed to remain in a mildly basic one such as provided by the 4-hydrocarbylaminomethyl side chain for a period of time with the application of heat furnished either by allowing the concentrated material to be heated for a short period of time after removal of the reaction solvent or by crystallization from a relatively high boiling solvent such as toluene or ethylacetate (Examples 9 and 10) and furan-2(3H)one cannot be isolated as it rearranges in situ to the 2-pyrrolidinone.

The novel compounds of Formula II are prepared by the following procedure:

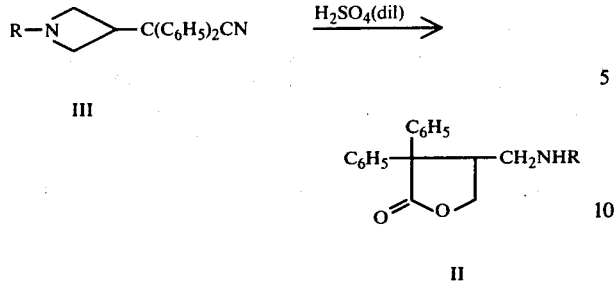

wherein R is as defined above.

According to the above procedure an α,α-diphenyl-α-(1-hydrocarbon-3-azetidinyl)acetonitrile is reacted with dilute sulfuric acid resulting in the formation of the 4,5-dihydrofuran-2-(3H)one ring. The novel reaction is usually carried out with the application of heat, e.g., at a temperature of from about 110° C. to about 140° C. for an extended period, e.g., of from about 35 hours to about 60 hours to effect the formation of the 4,5-dihydro-3,3-diphenyl-4-hydrocarbylaminomethylfuran-2(3H)one II from the α,α-diphenyl-α-(1-hydrocarbon-3-azetidinyl)acetonitrile. The product can be obtained from the reaction mixture by various methods but is preferably isolated by pouring the acidic reaction mixture onto ice, separation of the aqueous-organic layers, acid-base extraction of the organic layer and recrystallization of the 4,5-dihydrofuran-2(3H)one product from a suitable solvent.

The α,α-diphenyl-α-(1-hydrocarbon-3-azetidinyl)acetonitriles III are prepared from 1-hydrocarbon-3-azetidinols by the following procedure:

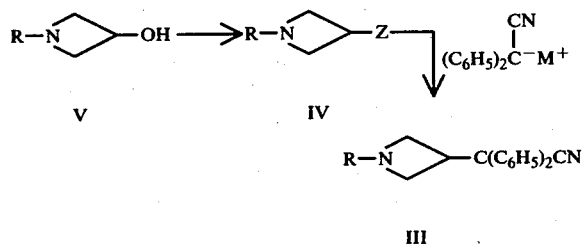

wherein R is as defined hereinabove, Z is a lower alkylsulfonyloxy radical, an arylsulfonyloxy radical or a halide radical, preferably chloride, and M+ is an alkali metal cation, preferably sodium or potassium.

According to the above procedure an alkyl or aryl sulfonate ester IV or an azetidinyl halide IV is prepared by methods known to the art. The alkali metal salt of diphenylacetonitrile is prepared in a similar solvent by reacting diphenylacetonitrile with an alkali metal hydride or an alkali metal amide. The sodium and potassium metal hydrides and amides are preferred. The solution of the alkyl or aryl sulfonate ester or the azetidinyl halide is then reacted with the alkali metal salt of diphenylacetonitrile at an elevated temperture, preferably at the reflux temperature of the organic solvent used. The α,α-diphenyl-α-(1-hydrocarbon-3-azetidinyl)acetonitrile III thusly prepared is isolated from the reaction mixture by known procedures and further purified by crystallization from a suitable solvent or solvents.

The 1-hydrocarbon-3-azetidinols are known compounds or they can be prepared as described by V. R. Gaertner, Tetrahedron Letters No. 39, pp. 4691-4 (1966), by Okutani et al., Chem. Pharm. Bull. 22 (7) 1490-7 (1974), or by procedures disclosed in U.S. Pat. No. 3,668,196.

The 1-hydrocarbon-3,3-diphenyl-4-halomethyl-2-pyrrolidinones of Formula VI

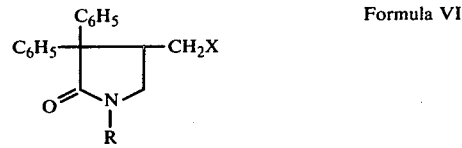

wherein R is as defined above and X is chloro, bromo or iodo are novel compounds and are readily prepared from the precursor hydroxy compounds. Thus, a 4-bromomethyl-3,3-diphenyl-1-isopropyl-2-pyrrolidinone can be prepared according to the procedure of Example 12 by substituting thionyl bromide for thionyl chloride. The 4-iodomethyl compound can be prepared by reacting a 4-chloromethyl compound with sodium iodide in acetone.

The α,α-diphenyl-α-(1-hydrocarbon-3-azetidinyl)acetonitriles disclosed herein as well as the α,α-diphenyl-α-(1-hydrocarbon-3-azetidinyl)acetamides prepared from them by partial hydrolysis in concentrated sulfuric acid have antiarrhythmic properties.

The following preparations and examples are not limiting but are illustrative of the compounds of this invention and processes for their preparation.

PREPARATION 1

α,α-Diphenyl-α-(1-isopropyl-3-azetidinyl)acetonitrile.

A mixture of 168 g. (0.87 mole) of diphenylacetonitrile and 40.42 g. (0.96 mole) of 57% sodium hydride in one liter of dry toluene was stirred at reflux temperature for three hours.

A stirred solution of 1-isopropyl-3-azetidinol (100 g., 0.87 mole) and 101 g. (1.0 mole) of triethylamine in 300 ml. of dry benzene was treated dropwise with 100 g. (0.87 mole) of methylsulfonyl chloride and after stirring for two hours at room temperature the mixture was filtered and the filter cake was washed with dry benzene.

The benzene solution of 1-isopropyl-3-azetidinylmethane sulfonate was added dropwise to the stirred refluxing toluene mixture containing the sodium salt of diphenylacetonitrile and refluxing continued for 1.5 hours after addition. The cooled reaction mixture was treated with water, the layers separated, and the organic layer extracted with dilute hydrochloric acid and water. The combined extracts were basified using dilute sodium hydroxide and the base insoluble material extracted with chloroform. The dried extract was concentrated and the residual material was recrystallized from isooctane. The α,α-diphenyl-α-(1-isopropyl-3-azetidinyl)acetonitrile weighed 142 g. (56%) and melted at 93°-95° C.

Analysis: Calcd. for $C_{20}H_{22}N_2$: C, 82.72; H, 7.64; N, 9.65. Found: C, 82.72; H, 7.73; N, 9.55.

PREPARATION 2

α,α-Diphenyl-α-(1-methyl-3-azetidinyl)acetonitrile.

A mixture of 4.0 g. (0.11 mole) of sodium amide, 21 g. (0.11 mole) of diphenylacetonitrile and 300 ml. of toluene was stirred at reflux for 4 hours in a nitrogen atmosphere. The heat was removed and an equimolar amount of 3-chloro-1-methylazetidine in toluene was added at a rate which maintained refluxing. The reaction mixture was refluxed an additional 4 hours, allowed to stand overnight at room temperature, washed with water and extracted with dilute hydrochloric acid. The aqueous acid extract was made basic with dilute sodium hydroxide, the base insoluble oil extracted with isopropyl ether, the ether extract dried over sodium sulfate and concentrated. The residual solid was recrystallized from ligroin to give 6.7 g. (27%) of product, m.p. 113°–115° C.

Analysis: Calcd. for $C_{18}H_{18}N_2$: C, 82.41; H, 6.92; N, 10.68. Found: C, 82.31; H, 6.98; N, 10.51.

PREPARATION 3

α-(1-Cyclohexyl-3-azetidinyl)-α,α-diphenylacetonitrile.

To 191 g. (1.0 mole) of 1-cyclohexyl-3-azetidinol hydrochloride in methylene chloride was added a dilute sodium hydroxide solution, the organic layer was extracted, dried (sodium sulfate), filtered and concentrated in vacuo. The residue was dissolved in dry benzene and stirred with 116 g. (1.05 mole) of triethylamine and cooled with an ice bath. One mole (115 g.) of methanesulfonylchloride was added, dropwise, and stirring was continued at room temperature for three hours and the mixture was filtered. The filtrate was added at a fast dropwise rate to a reaction mixture of 50.0 g. (1 mole) of sodium hydride in one liter of dry toluene to which 193 g. (1 mole) of diphenylacetonitrile had been added slowly at 45°–50° C. and had already stirred at reflux for two hours. After addition was complete, reflux was continued for two hours, and the solution was stirred overnight. An equivalent amount of isooctane was added, and after extracting four times with a dilute hydrochloric acid solution, the acid layers were combined and made basic with 50% sodium hydroxide, with ice cooling, and extracted with chloroform. The organic layer was dried, filtered and concentrated in vacuo. The solid which formed when the residue was treated with isopropyl ether was recrystallized from isopropyl ether twice. The product weighed 58.0 g. (18% yield) and melted at 111°–114° C.

Analysis: Calculated for $C_{23}H_{26}N_2$: C, 83.59; H, 7.93; N, 8.48. Found: C, 83.24; H, 7.94; N, 8.27.

PREPARATION 4

α,α-Diphenyl-α-[1-(1-phenylethyl-3-azetidinyl)-]acetonitrile.

To a solution of 67.9 (0.67 mole) of triethylamine and 114 g. (0.64 mole) of 1-(1-phenylethyl)-3-azetidinol in 800 ml. of dry benzene was added dropwise 73.6 g. (0.65 mole) of methane sulfonyl chloride while cooling with an ice bath. After stirring for 2 hours at room temperature the mixture was filtered. Over a period of 40 minutes the filtrate was added dropwise to a refluxing suspension of the sodium salt of diphenyl acetonitrile prepared by refluxing 123.5 g. (0.64 mole) of the nitrile and 28.2 g. (0.7 mole) of 57% sodium hydride in one liter of dry toluene for 2.5 hrs. The resulting solution was refluxed 2 hrs. and extracted with water. The toluene solution was extracted with dilute hydrochloric acid. Very little of the desired product went into the aqueous layer. The toluene was treated with water, followed by a volume of isooctane equal to the toluene causing an oil layer to form which was separated with the water layer. The toluene was washed several times and all aqueous layers combined. The aqueous-oil mixture was made basic with dilute sodium hydroxide and extracted with chloroform, which was dried (sodium sulfate) and concentrated. The residue was recrystallized from isooctane-isopropyl ether to give 94 g. (42%) of product melting at 122°–130° C. A 10 g. sample was recrystallized from the same solvent to give 7.8 g. of product melting at 130°–132° C.

Analysis: Calculated for $C_{25}H_{24}N_2$: C, 85.19; H, 6.86; N, 7.95. Found: C, 84.98; H, 6.84; N, 7.83.

PREPARATION 5

In the manner of the preceding discussion and in accordance with Preparations 1–4 starting with the appropriate 1-hydrocarbon-3-azetidinol and diphenylacetonitrile, the following α,α-diphenyl-α-(1-hydrocarbon-3-azetidinyl)acetonitriles are produced:

α,α-diphenyl-α-(1-ethyl-3-azetidinyl)acetonitrile from 1-ethyl-3-azetidinol and diphenylacetonitrile;

α,α-diphenyl-α-(1-propyl-3-azetidinyl)acetonitrile from 1-propyl-3-azetidinol and diphenylacetonitrile;

α,α-diphenyl-α-(1-butyl-3-azetidinyl)acetonitrile from 1-butyl-3-azetidinol and diphenylacetonitrile;

α,α-diphenyl-α-(1-isobutyl-3-azetidinyl)acetonitrile from 1-isobutyl-3-azetidinol and diphenylacetonitrile;

α,α-diphenyl-α-(1-benzyl-3-azetidinyl)acetonitrile from 1-benzyl-3-azetidinol and diphenylacetonitrile; and α,α-diphenyl-α-(1-phenethyl-3-azetidinyl)acetonitrile from 1-phenethyl-3-azetidinol and diphenylacetonitrile.

EXAMPLE 1

4,5-Dihydro-3,3-diphenyl-4-isopropylaminomethylfuran-2-(3H)one.

α,α-Diphenyl-α-(1-isopropyl-3-azetidinyl)acetonitrile (142 g.; 0.49 mole) was added to 500 g. of 70% sulfuric acid at 90°–100° C. The temperature was raised to 130° C. for 48 hours. The cooled mixture was poured onto ice and the cold mixture made basic ty the addition of solid sodium hydroxide. The basic mixture was extracted with chloroform and the combined chloroform extracts dried over sodium sulfate and concentrated. The residual material was crystallized from an 80% isooctane — 20% isopropyl ether solution. The 4,5-dihydro-3,3-diphenyl-4-isopropylaminomethylfuran-2(3H)one weighed 105 g. (69.3%) and melted at 78°–80° C.

Analysis: Calcd. for $C_{20}H_{23}NO_2$: C, 77.64; H, 7.49; N, 4.53. Found: C, 77.68; H, 7.36; N, 4.23.

EXAMPLE 2

4,5-Dihydro-3,3-diphenyl-4-methylaminomethylfuran-2-(3H)one Maleate.

Sixty-four grams (0.24 mole) of α,α-diphenyl-α-(1-methyl-3-azetidinyl)acetonitrile was dissolved in 300 g. of 70% sulfuric acid solution at 110°–120° C. The solution was heated to 130° C. for 48 hours, poured into ice, and made basic with the addition of sodium hydroxide while continuing to cool by adding ice. The mixture was extracted with chloroform, the combined extracts dried, filtered, and concentrated in vacuo. The residual oil was dissolved in isopropanol and treated with 28.0 g. of maleic acid. The maleate salt was recrystallized from ethanol-dimethylformamide. The dried maleate salt weighed 58.0 g. and melted at 189°–192° C.

Analysis: Calcd. for $C_{22}H_{23}NO_6$: C, 66.49; H, 5.83; N, 3.53. Found: C, 65.97; H, 5.90; N, 3.79.

EXAMPLE 3

4,5-Dihydro-4-cyclohexylaminomethyl-3,3-diphenylfuran-2(3H)one.

To 41.0 g. (0.12 mole) of α-(1-cyclohexyl-3-azetidinyl)-α,α-diphenylacetonitrile was added 100 g. of a 70% solution of sulfuric acid, and the mixture was stirred and heated at 120° C. for 48 hrs. The solution was then poured over ice and made basic with 50% sodium hydroxide, and extracted with chloroform. The organic layer was dried, filtered, and concentrated in vacuo. The residue was crystallized twice from isopropyl ether, the crystallized material weighed 8.0 g. (20% yield) and melted at 129°–131° C.

Analysis: Calculated for $C_{23}H_{27}NO_2$: C, 79.05; H, 7.79; N, 4.01. Found: C, 78.80; H, 7.80; N, 3.91.

EXAMPLE 4

4,5-Dihydro-3,3-diphenyl-4-(1-phenylethylaminomethyl)furan-2(3H)one Maleate.

4,5-Dihydrate-3,3-diphenyl-4-(1-phenylethylaminomethyl)furan-2(3H)one was prepared following the procedures described in the previous examples from α-[1-(1-phenylethyl-3-azetidinyl)]-α,α-diphenylacetonitrile. The maleate salt melting at 190°–192° C. was prepared from the free base.

EXAMPLE 5

In the manner of the preceding discussion and in accordance with Examples 1–3 starting with the appropriate α,α-diphenyl-α-(1-hydrocarbon-3-azetidinyl)acetonitrile and dilute sulfuric acid, the following 4,5-dihydro-3,3-diphenyl-4-hydrocarbylaminomethylfuran-2-(3H)ones are produced:

4,5-dihydro-3,3-diphenyl-4-ethylaminomethylfuran-2-(3H)one from α,α-diphenyl-α-(1-ethyl-3-azetidinyl)acetonitrile and dilute sulfuric acid;

4,5-dihydro-3,3-diphenyl-4-propylaminomethylfuran-2-(3H)one from α,α-diphenyl-α-(1-propyl-3-azetidinyl)acetonitrile and dilute sulfuric acid;

4,5-dihydro-3,3-diphenyl-4-isobutylaminomethylfuran-2-(3H) one from α,α-diphenyl-α-(1-isobutyl-3-azetidinyl)acetonitrile and dilute sulfuric acid;

4,5-dihydro-3,3-diphenyl-4-benzylaminomethylfuran-2-(3H)one from α,α-diphenyl-α-(1-benzyl-3-azetidinyl)acetonitrile and dilute sulfuric acid; and 4,5-dihydro-3,3-diphenyl-4-phenethylaminoethylfuran-2-(3H)one from α,α-diphenyl-α-(1-phenethyl-3-azetidinyl)acetonitrile and dilute sulfuric acid.

EXAMPLE 6

3,3-Diphenyl-4-hydroxymethyl-1-isopropyl-2-pyrrolidinone.

Fifty-three grams (0.17 mole) of 4,5-dihydro-3,3-diphenyl-4-isopropylaminomethylfuran-2-(3H)one was dissolved in 300 ml. of boiling isooctane and 0.25 g. of 67% sodium hydride added. After refluxing for 6.5 hours an additional 0.25 g. of 57% sodium hydride was added and refluxing was continued overnight. The cooled mixture was filtered and the solid was recrystallized from toluene. The 3,3-diphenyl-4-hydroxymethyl-1-isopropyl-2-pyrrolidinone weighed 42 g. (80%) and melted at 159°–161° C. Analysis: Calcd. for $C_{20}H_{23}NO_2$: C, 77.64; H, 7.49; N, 4.53. Found: C, 77.71; H, 7.52; N, 4.37.

EXAMPLE 7

1-Cyclohexyl-4-hydroxymethyl-3,3-diphenyl-2-pyrrolidinone.

To 90.0 g. (0.26 mole) of 4-cyclohexylaminomethyl-4,5-dihydro-3,3-diphenylfuran-2-(3H)one in 500 ml. of isooctane was added 1.0 g. of sodium hydride (57% in mineral oil) as a catalyst and the mixture was refluxed overnight. Upon cooling a solid precipitated and the isooctane was decanted from the solid. The solid was recrystallized from isopropyl alcohol, weighed 66.0 g. (73% yield) and melted at 148°–150° C.

Analysis: Calcd. for $C_{23}H_{27}NO_2$: C, 79.05; H, 7.79; N, 4.01. Found: C, 78.97; H, 7.74; N, 3.92.

EXAMPLE 8

4-Hydroxymethyl-3,3-diphenyl-1-(1-phenylethyl)-2-pyrrolidinone.

Two hundred grams of 4,5-dihydro-4-(1-phenylethylaminomethyl)-3,3-diphenylfuran-2(3H)one maleate was partitioned between isopropyl ether and a dilute sodium hydroxide solution, the ether layer dried, filtered and concentrated in vacuo. Fifty grams (0.13 mole) of the residue was dissolved in hot isooctane with 1 g. of sodium hydride (50% in mineral oil) as a catalyst and refluxed overnight. The isooctane was decanted from the cooled liquid-solid mixture and the residue was recrystallized from a 90:10 mixture of isopropyl ether-:isopropanol. The solid weighed 34.0 g. (70% yield) and melted at 130°–144° C.

Analysis: Calcd. for $C_{25}H_{25}NO_2$: C, 80.83; H, 6.78; N, 3.77. Found: C, 80.80; H, 6.85; N, 3.66.

EXAMPLE 9

4-Hydroxymethyl-1-methyl-3,3-diphenyl-2-pyrrolidinone.

Forty grams (0.153 mole) of α,α-diphenyl-α-(1-methyl-3-azetidinyl)acetonitrile was heated in 150 g. of 70% sulfuric acid solution for 48 hrs. at 130° C. The reaction mixture was poured onto ice and made basic with a 50% sodium hydroxide solution while cooling with the addition of more ice. This mixture was extracted with chloroform, combined extracts dried, filtered, and concentrated in vacuo. The residue was crystallized from toluene, weighed 34.5 g. and melted at 148°–150° C. Ten grams was recrystallized twice from toluene, weighed 7.5 g., and melted at 149°–151° C.

Analysis: Calcd. for $C_{18}H_{19}NO_2$: C, 76.84; H, 6.81; N, 4.98. Found: C, 76.81; H, 6.81; N, 4.93.

EXAMPLE 10

4-(Hydroxymethyl)-3,3-diphenyl-2-pyrrolidinone.

To 750 ml. of methanol and 80.0 g. (0.22 mole) of 4-(1-phenylethylaminomethyl)-4,5-dihydro-3,3-diphenylfuran-2(3H)one was added 3.0 g. of palladium hydroxide catalyst and the mixture was shaken in three atmospheres of hydrogen at 70° C. for 18 hrs. Upon filtering starting material was found to be present; fresh catalyst was added to the solution which was shaken in three atmospheres of hydrogen at 70° C. for three more hours. After filtering the filtrate was concentrated in vacuo. The residue was dissolved in 100 ml. of ethyl acetate, and 100 ml. of isopropyl ether was added. A portion of the crystallized material was recrystallized from the same solvent system to give product melting at 145°–148° C.

Analysis: Calcd. for $C_{17}H_{17}NO_2$: C, 76.38; H, 6.41; H, 5.24. Found: C, 76.22; H, 6.49; N, 5.17.

EXAMPLE 11

In the manner of the preceding discussion and in accordance with Examples 6–8 starting with the appropriate 4,5-dihydro-3,3-diphenyl-4-hydrocarbylaminomethylfuran-2-(3H)one and sodium hydride, the following 3,3-diphenyl-4-hydroxymethyl-1-hydrocarbon-2-pyrrolidinones are produced:

3,3-diphenyl-4-hydroxymethyl-1-ethyl-2-pyrrolidinone from 4,5-dihydro-3,3-diphenyl-4-ethylaminomethylfuran-2-(3H)one and sodium hydride;

3,3-diphenyl-4-hydroxymethyl-1-propyl-2-pyrrolidinone from 4,5-dihydro-3,3-diphenyl-4-propylaminomethylfuran-2-(3H)one and sodium hydride;

3,3-diphenyl-4-hydroxymethyl-1-butyl-2-pyrrolidinone from 4,5-dihydro-3,3-diphenyl-4-butylaminomethylfuran-2-(3H)one and sodium hydride;

3,3-diphenyl-4-hydroxymethyl-1-isobutyl-2-pyrrolidinone from 4,5-dihydro-3,3-diphenyl-4-isobutylaminomethylfuran-2-(3H)one and sodium hydride;

3,3-diphenyl-4-hydroxymethyl-1-benzyl-2-pyrrolidinone from 4,5-dihydro-3,3-diphenyl-4-benzylaminomethylfuran-2-(3H)one and sodium hydride, and 3,3-diphenyl-4-hydroxymethyl-1-phenethyl-2-pyrrolidinone from 4,5-dihydro-3,3-diphenyl-4-phenethylaminomethylfuran-2-(3H)one and sodium hydride.

EXAMPLE 12

4-Chloromethyl-3,3-diphenyl-1-isopropyl-2-pyrrolidinone.

A solution of 43 g. (0.14 mole) of 3,3-diphenyl-4-hydroxymethyl-1-isopropyl-2-pyrrolidinone in 250 ml. of chloroform was treated with 33 g. (0.28 mole) of thionyl chloride over a one minute period followed by the dropwise addition of 22 g. (0.23 mole) of pyridine over a 30 minute period. The mixture was refluxed 18 hours and then poured onto ice. The cold mixture was made basic by the addition of sodium hydroxide. The chloroform layer was separated, dried over sodium sulfate and concentrated. The residue was crystallized using charcoal from a 25% ethyl acetate — 75% isopropyl ether mixture. The crystalline solid was recrystallized from a 75% ethanol — 25% water mixture and then from isopropyl ether. The dried 4-chloromethyl-3,3-diphenyl-1-isopropyl-2-pyrrolidinone weighed 23 g. and melted at 114°–116° C.

Analysis: Calcd. for $C_{20}H_{22}NOCl$: C, 73.27; H, 6.76; N, 4.27. Found: C, 73.30; H, 6.82; N, 4.22.

EXAMPLE 13

4-Chloromethyl-1-methyl-3,3-diphenyl-2-pyrrolidinone.

To 25.0 g. (0.09 mole) of 4-hydroxy-1-methyl-3,3-diphenyl-2-pyrrolidinone, in 200 ml. of chloroform was added 21.4 g. (0.18 mole) of thionyl chloride. With stirring and ice bath cooling, 18.0 g. (0.23 mole) of pyridine was added dropwise. The solution was refluxed for two hours. After concentrating in vacuo, the residue was dissolved in chloroform and washed successively with dilute hydrochloric acid solution and dilute sodium hydroxide. The chloroform solution was dried, filtered, and concentrated in vacuo. The solid residue was recrystallized from a 50:50 ethyl acetate-isopropyl ether mixture. It weighed 16.0 g. (59% yield) and melted at 120°–122° C.

Analysis: Calcd. for $C_{18}H_{18}ClNO$: C, 72.11; H, 6.05; N, 4.67. Found: C, 71.83; H, 6.04; N, 4.72.

EXAMPLE 14

4-Chloromethyl-1-cyclohexyl-3,3-diphenyl-2-pyrrolidinone.

To 60.0 g. (0.17 mole) of 1-cyclohexyl-4-hydroxymethyl-3,3-diphenyl-2-pyrrolidinone, in 400 ml. of chloroform was added 48.0 g. (0.40 mole) of thionylchloride with stirring. To this solution was added dropwise with ice bath cooling 40 g. (0.52 mole) of dry pyridine and the solution was refluxed for two hours. After concentrating in vacuo the residue was dissolved in chloroform and washed successively with dilute hydrochloric acid solution and dilute sodium hydroxide solution. The chloroform solution was dried (sodium sulfate), filtered, and concentrated in vacuo. The residue was recrystallized from isopropyl ether and after drying weighed 34.5 g. (55% yield) and melted at 124°–126° C.

Analysis: Calculated for $C_{23}H_{26}ClNO$: C, 75.09; H, 7.12; N, 3.81. Found: C, 74.73; H, 7.12; N, 3.75.

EXAMPLE 15

4-(Chloromethyl)-3,3-diphenyl-1-(1-phenylethyl)-2-pyrrolidinone.

To 34.0 g. (0.09 mole) of 4-(hydroxymethyl)-3,3-diphenyl-1-(1-phenylethyl)-2-pyrrolidinone in 200 ml. of chloroform was added 25.0 g. (0.20 mole) of thionylchloride. To this solution with stirring and ice bath cooling was added dropwise, 20.0 g. (0.26 mole) of dry pyridine maintaining the reaction mixture at 25° C. The solution was refluxed for 1.5 hours, concentrated in vacuo and the residue was dissolved in chloroform. The solution was washed successively with dilute hydrochloric acid solution and dilute sodium hydroxide solution. The chloroform solution was dried, filtered, and concentrated in vacuo. The residue was dissolved in hot isopropyl ether and some isooctane was added. The hot solution was decanted from a gummy residue and the product crystallized from the cooled solution. Seven grams were recrystallized in isopropyl ether to give the product which melted at 115°–120° C.

Analysis: Calcd. for $C_{28}H_{24}ClNO$: C, 77.01; H, 6.20; N, 3.59. Found: C, 77.11; H, 6.31; N, 3.55.

EXAMPLE 16

4-(Chloromethyl)-3,3-diphenyl-2-pyrrolidinone.

To 30.0 g. (0.11 mole) of 4-(hydroxymethyl)-3,3-diphenyl-2-pyrrolidinone in 200 ml. of chloroform was added 25.0 g. (0.20 mole) of thionyl chloride. To this stirring solution was added dropwise with ice bath cooling 20.0 g. (0.26 mole) of dry pyridine maintaining room temperature. The solution was refluxed for 2.5 hours. Upon cooling, the chloroform solution was washed successively with dilute hydrochloric acid solution and dilute sodium hydroxide solution. The chloroform was dried, filtered and concentrated in vacuo. The solid residue was recrystallized twice from ethyl acetate-isopropanol to give product melting at 218°–219° C.

Analysis: Calcd. for $C_{17}H_{16}ClNO$: C, 71.45; H, 5.64; N, 4.90. Found: C, 71.22; H, 5.60; N, 4.91.

I claim:

1. A process for the production of a 4-hydroxymethyl-2-pyrrolidinone having the formula

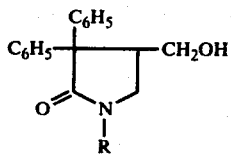

wherein R is selected from the group consisting of hydrogen, lower alkyl having one to six carbon atoms, lower cycloalkyl having four to eight carbon atoms or phenyllower alkyl consisting of benzyl, phenethyl, phenpropyl and α-methylbenzyl which comprises mixing a 4,5-dihydrofuran-2(3H)one of the formula

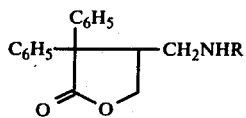

wherein R is as defined above with a catalytic amount of a strong base to cause intramolecular rearrangement of the 4,5-dihydrofuran-2(3H)one to the 4-hydroxymethyl-2-pyrrolidinone.

* * * * *